United States Patent [19]

Seidelbach

[11] Patent Number: 6,166,277
[45] Date of Patent: Dec. 26, 2000

[54] PROCESS FOR EVAPORATING 1,2-DICHLOROETHANE (EDC)

[75] Inventor: Friedrich Seidelbach, Wiesbaden, Germany

[73] Assignee: Krupp Uhde GmbH, Dortmund, Germany

[21] Appl. No.: 09/467,450

[22] Filed: Dec. 20, 1999

[30] Foreign Application Priority Data

Dec. 22, 1998 [DE] Germany ............... 198 59 262

[51] Int. Cl.⁷ .................................. C07C 17/25
[52] U.S. Cl. ........................... 570/226; 570/230
[58] Field of Search ..................... 570/226, 230

[56] References Cited

U.S. PATENT DOCUMENTS

| | | | |
|---|---|---|---|
| 4,788,357 | 11/1988 | Dummer et al. | 570/226 |
| 4,960,963 | 10/1990 | Teshima et al. | 570/226 |
| 5,488,190 | 1/1996 | Blevec et al. | . |
| 5,728,906 | 3/1998 | Eguchi et al. | 570/226 |

*Primary Examiner*—Alan Siegel
*Attorney, Agent, or Firm*—Rosenman & Colin, LLP

[57] ABSTRACT

A process for evaporating 1, 2-dichloroethane (EDC) prior to its thermal decomposition (pyrolysis) is provided so that it facilitates the heating of the liquid-phase EDC at temperatures below 100° C. to meet the inlet conditions for the pyrolysis zone, while dispensing with the need for an evaporation zone and exploiting sensible heat recovery at the same time. This is achieved in that the liquid-phase EDC is first pressurized to attain a value above its critical pressure (5.36 MPa) and then heated to attain at least its critical temperature (approx. 288° C.).

5 Claims, 1 Drawing Sheet

PROCESS FOR EVAPORATING 1,2-DICHLOROETHANE (EDC)

FIELD OF INVENTION

The invention relates to a process for evaporating 1,2-dichloroethane (EDC) prior to its thermal decomposition (pyrolysis).

BACKGROUND OF INVENTION

Mainly, technical-grade vinyl chloride (VCM) is produced by the non-catalytic and incomplete thermal decomposition (pyrolysis) of gaseous 1,2-dichloroethane (EDC), in the course of which hydrogen chloride (HCl) is formed as a coupled product.

EP-0276775-B1 discloses that standard commercial, non-catalytic processes are performed at a pressure of below 1 to 3 Mpa and at a pyrolysis zone outlet temperature of 450° C. to 600° C. The inlet temperatures in the pyrolysis zone range from 200° C. to 300° C.

In U.S. Pat. No. 5,488,190 a process is described which prevents the formation of by-products during the pyrolysis of EDC, the heat being transferred via a tube wall in direct contact with a gaseous or solid matter which has been admixed with the EDC and heated to a high temperature. During this process, the EDC is only evaporated in the subcritical pressure and temperature range.

DE-A 35 43 222 describes an improved process for producing vinyl chloride by thermally cracking 1,2-dichloroethane to obtain gaseous EDC from liquid EDC in the subcritical range, as can be seen in FIG. 1 of the patent.

In the commercial process, the pyrolysis zone is designed as a burner which is heated with natural gas or fuel oil. The burner's combustion chamber has one or more tube coils in which EDC pyrolysis occurs.

The residence time in the pyrolysis zone and the temperature are selected to ensure that on the one hand, as few undesirable by-products as possible are formed, such as soot (coke), chlorinated and unsaturated hydrogen chlorides and benzole, and on the other hand, to ensure for economic reasons, that the EDC yield is at least 50%

The cause of soot formation can by no means be solely ascribed to the relatively high temperatures in the pyrolysis zone in standard commercial processes. The EDC, which is usually in liquid phase, is evaporated and superheated if necessary, prior to pyrolysis.

Evaporators and, for example, boiling reactors have a decidedly unfavorable residence time pattern as regards substances which have a tendency to decompose as in agitated boilers. As a result, precursors, which encourage soot formation, are formed during EDC evaporation before the EDC reaches the actual pyrolysis zone.

This is substantiated, for example, by the fact that in the known process, which involves cracked gas heating and external evaporation (heat recovery) and which is applied in the EDC/VDM production plants constructed by the patent applicant, a blow-down flow must be continually drawn off to prevent premature contamination of the evaporator and the pyrolysis tubes. The blow-down flow contains decomposition products which are rich in carbon and which have coalesced to form larger particles.

SUMMARY OF THE INVENTION

The objective of the invention is to provide a solution with which it is possible to heat the liquid-phase EDC at temperatures below 100° C. so that it meets the inlet conditions for the pyrolysis zone, whilst dispensing with the need for an evaporation zone and exploiting sensible heat recovery at the same time.

With a process such as the one described in the introduction, the invention realizes this objective in that the liquid-phase EDC is first pressurized to attain a value above its critical pressure (5.36 Mpa) and then heated to attain at least its critical temperature (approx. 288° C.).

The invention removes the need for the EDC to pass through an evaporation zone and thus avoids the formation of the above-mentioned precursors which encourage soot formation. In so doing, the invention makes use of the discovery that the curve plotting the isenthalpic change of phase in a pressure/temperature chart displays a comparatively pronounced bend in the vicinity of the critical point. It is then also possible, as provided for by one embodiment of the invention, to effect an interim expansion of the heated EDC feedstock and then reheat it; the EDC pressure being subsequently reduced to conform with the inlet conditions of the pyrolysis zone which dictate that the EDC is gaseous at temperatures in excess of 200° C.

The invention provides for the caloric content of the cracked gas leaving the pyrolysis zone to be used to heat the supercritical fluid. In accordance with the invention, this can be effected in a simple countercurrent heat exchanger.

The favourable residence times in the countercurrent heat exchanger constitute a further positive aspect of the invention. A residence time pattern conforming to the flow tube principle is facilitated on both sides and prevents the formation of harmful soot/precursors. This in turn considerably reduces the formation of soot overall.

BRIEF DESCRIPTION OF THE DRAWING

The above and other objects and features of the invention will become apparent from the following description of preferred embodiments, in conjunction with the accompanying drawing in which.

DETAILED DESCRIPTION OF THE PREFERRED EMBODIMENTS

Figure 1:
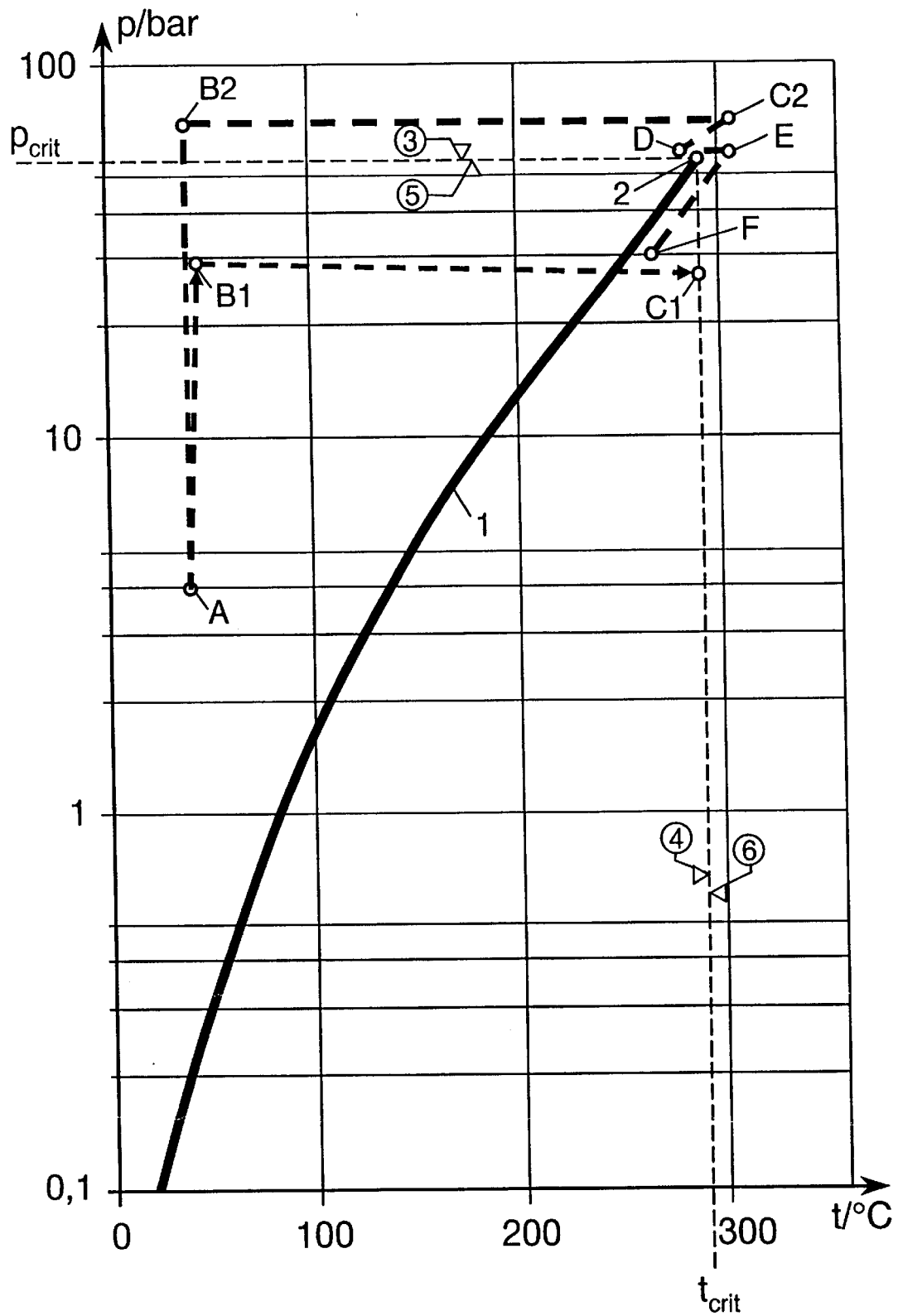
FIG. 1 represents the 1,2-EDC evaporation curve to the critical point. The thin broken line shows the process in accordance with EP-0 276 775-B1 and the bold broken line shows the process in accordance with the invention.

Referring to FIG. 1, a phase diagram for pure EDC is also shown in FIG. 1. The temperature T is shown on the abscissa and the pressure p is shown on the ordinate. In this p/T chart, 1 represents the EDC's vapour pressure curve. The vapour pressure curve (1) ends at the EDC's critical point 2. The p/T conditions, under which the EDC is in liquid phase, are shown in the area above the vapour pressure curve and the gaseous/vaporous EDC is shown below the curve (1). If EDC conditions are actually contiguous to the vapour pressure curve (1), the vapour and the liquid phase coexist. If both EDC phase variables—i.e. both the pressure and the temperature—assume values above the critical values ($p_{crit}$=53.6 bar, $t_{crit}$≈288° C.), the EDC takes on the form of a so-called supercritical medium. A supercritical medium has a similarly high density to that of the liquid phase, but in contrast to the liquid phase, cannot develop an interface/adjacent surface.

In the phase diagram, the ordinate $p_{crit}$ separates the liquid area (5) from the area representing the EDC fluid at supercritical pressure (3). Similarly, the abscissa $t_{crit}$ separates the area showing the superheated EDC vapour (4) from the area representing the EDC fluid at supercritical temperature (6).

The continuous line A-B1-C1, in the phase diagram describes the known production of supercritical EDC vapour in accordance with EP 0 276 775-B1. The pressure of the EDC liquid is brought into line with the evaporation pressure between A and B1. From B1 to C1 the EDC liquid is preheated to the boiling temperature. The EDC evaporation is shown at the point of intersection with the vapour pressure curve (1) and EDC superheating finally occurs between the vapour pressure curve and C1.

In contrast, the production of supercritical EDC liquid in accordance with the invention is shown along the continuous line A-B2-C2. The pressure of the EDC liquid is raised to supercritical pressure between A and B2. From B2 to C2, the EDC fluid at the supercritical pressure is heated to a supercritical temperature and the EDC fluid, which is supercritical with regard to pressure and temperature, is formed.

No phase transitions occur during the heating process, and for this reason, the conveyance variables of the EDC undergo constant, but not erratic, changes. For example, the EDC continues to be able to dissolve impurities, the concentration of these substances being the same in both the fluid EDC and the liquid feed EDC. This ensures from the outset that the concentration of such escort substances does not increase, whereas in contrast, the concentration of individual escort substances always increases in the non-evaporated part of the liquid during the formation of EDC vapour at the liquid phase surface. This is a further advantage of the process in accordance with the invention.

If the EDC, which is heated in accordance with the invention, is to be converted from a fluid phase to an initial state (which more or less corresponds to the initial state of the superheated EDC vapour produced by evaporation using the known method), then the fluid EDC must undergo a double flashing cycle along the line C2-D-E-F with interim heating D-E.

While the invention has been described with respect to the particular embodiments, it will be apparent to those skilled in the art that various modifications and changes may be made, without departing from the spirit and scope of the invention as defined in the following claims:

What is claimed is:

1. A process for the thermal decomposition of 1,2-dichloroethane including evaporating said 1,2-dichloroethane (EDC) prior to its thermal decomposition (pyrolysis), said process comprising the step of:

(a) pressuring the liquid-phase EDC to attain a value above its critical pressure (5.36 MPa); and (b) heating the EDC to attain at least its critical temperature (approx. 288° C.).

2. The process in accordance with claim 1, further comprising the step of subjecting the EDC, which is heated to at least its critical temperature, to interim expansion and to reheating.

3. The process in accordance with 1 or 2, further comprising the step of relaxing the EDC to meet the inlet conditions for the pyrolysis zone with temperatures of 150° C. to 400° C. and pressure of 1 to 10 MPa.

4. The process in accordance with claim 1, wherein the caloric content of the cracked gas leaving the pyrolysis zone is used to heat the supercritical fluid.

5. The process in accordance with claim 1, wherein a countercurrent heat exchanger is used to heat the supercritical EDC.

* * * * *